United States Patent
Meter

(10) Patent No.: US 11,766,029 B2
(45) Date of Patent: Sep. 26, 2023

(54) METHOD FOR PRODUCING CHICKEN INCLUDING DETERMINING THE GENDER OF CHICKEN EMBRYOS

(71) Applicant: SELEGGT GmbH, Cologne (DE)

(72) Inventor: Tjitze Meter, Veenendaal (NL)

(73) Assignee: SELEGGT GmbH, Cologne (DE)

( * ) Notice: Subject to any disclaimer, the term of this patent is extended or adjusted under 35 U.S.C. 154(b) by 530 days.

(21) Appl. No.: 16/628,706

(22) PCT Filed: Jul. 6, 2017

(86) PCT No.: PCT/EP2017/067029
§ 371 (c)(1),
(2) Date: Jan. 6, 2020

(87) PCT Pub. No.: WO2019/007520
PCT Pub. Date: Jan. 10, 2019

(65) Prior Publication Data
US 2020/0187462 A1 Jun. 18, 2020

(51) Int. Cl.
A01K 45/00 (2006.01)
A01K 41/00 (2006.01)
A01K 67/02 (2006.01)

(52) U.S. Cl.
CPC ............ A01K 45/007 (2013.01); A01K 41/00 (2013.01); A01K 67/02 (2013.01)

(58) Field of Classification Search
CPC ....... A01K 45/007; A01K 41/00; A01K 67/02
USPC .......................................................... 119/68
See application file for complete search history.

(56) References Cited

U.S. PATENT DOCUMENTS

| 5,699,751 | A | * | 12/1997 | Phelps | A01K 45/007 |
| | | | | | 119/6.8 |
| 6,365,339 | B1 | | 4/2002 | Daum et al. | |
| 6,510,811 | B1 | | 1/2003 | Gore et al. | |
| 7,617,795 | B2 | * | 11/2009 | Wolfe | A01K 45/007 |
| | | | | | 119/6.8 |
| 9,686,969 | B2 | * | 6/2017 | Meissner | A01K 43/04 |

(Continued)

FOREIGN PATENT DOCUMENTS

| CA | 2339862 A1 * | 4/2000 | ............. A01K 45/00 |
| DE | 102015226490 A1 * | 6/2017 | ............. G01N 33/08 |

(Continued)

OTHER PUBLICATIONS

Moreira De Souza: "Basic Aspects of In-Ovo Injection in Commercial Hatcheries", Feb. 19, 2013, Retrieved from the Internet: URL:http://WWW.thepoultrysite.com/focus/contents/ceva/OnlineBulletins/ob_2008/Article-No20-Sept08.pdf.

(Continued)

Primary Examiner — Ebony E Evans
(74) Attorney, Agent, or Firm — N.V. Nederlandsch Octrooibureau

(57) ABSTRACT

The present invention relates to a method for producing poultry, in particular chicken, the method comprising;
  a) incubating a batch of eggs in an incubating device during a first incubating period of between about 7 to about 11 days, and then,
  b) maintaining an egg in a predetermined sampling position during a settling time for allowing allantoic fluid to surface,
  c) determining a location of entry based on one or more egg parameters.

20 Claims, 4 Drawing Sheets

(56) References Cited

U.S. PATENT DOCUMENTS

Figure 1:
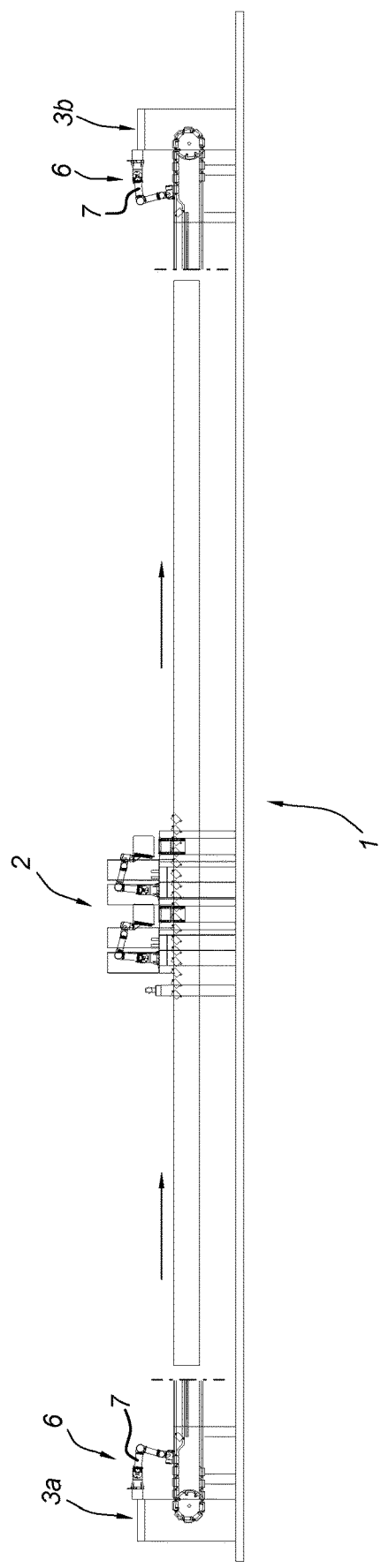

| | | | | |
|---|---|---|---|---|
| 2019/0166805 A1* | 6/2019 | Einspanier | ............. | G01N 33/08 |
| 2023/0045391 A1* | 2/2023 | Stutterheim | ......... | G01N 33/085 |

FOREIGN PATENT DOCUMENTS

| | | | | |
|---|---|---|---|---|
| DE | 102016215127 A1 | 2/2018 | | |
| EP | 1122997 B1 | 6/2004 | | |
| EP | 3017695 | 5/2016 | | |
| EP | 3017695 A1 * | 5/2016 | ............. | A01K 43/00 |
| WO | 9814781 | 4/1998 | | |
| WO | WO-9814781 A1 * | 4/1998 | ............. | A01K 43/00 |
| WO | WO-9913709 A1 * | 3/1999 | ........... | A01K 45/007 |
| WO | WO-2009067264 A1 * | 5/2009 | ........... | A01K 45/007 |
| WO | WO-2012088471 A * | 6/2012 | ......... | A61B 17/3403 |
| WO | 2014021715 A2 | 2/2014 | | |
| WO | WO-2014021715 A2 * | 2/2014 | ............. | A01K 43/00 |
| WO | WO-2016039621 A1 * | 3/2016 | ............. | A01K 43/00 |
| WO | WO-2017109133 A1 * | 6/2017 | ............. | G01N 21/78 |
| WO | WO-2018029096 A1 * | 2/2018 | ............. | A01K 43/00 |

OTHER PUBLICATIONS

"Site of Injection Crucial to In Ovo Vaccination", Zoetis, Jul. 23, 2009, Retrieved from the Internet: URL:http://news.zoetis.com/press-release/poultry/site-inject!on-crucial-ovo-vaccination.

* cited by examiner

METHOD FOR PRODUCING CHICKEN INCLUDING DETERMINING THE GENDER OF CHICKEN EMBRYOS

FIELD OF THE INVENTION

The present invention relates to a method for producing chicken. The method includes incubating eggs in an incubating device and determining the gender of chicken embryo's.

BACKGROUND ART

It is generally known to incubate eggs in incubation devices, which substantially comprise a cabinet with climate control. The eggs that are to be incubated are placed in the cabinet. In general, during incubation the eggs are turned at regular intervals, inter alia in order to prevent the embryos from sticking to the membranes. After incubating, the eggs are placed in a second cabinet in order ultimately to be hatched therein, that is the chicks emerging from the egg.

Determining the gender of the chicken embryo in the egg based on the presence of a gender specific compound in the allantoic fluid sample, is known per se. For example, WO9814781A1 relates to a method of determining the gender of a bird in ovo and comprises detecting the presence or absence of an elevated level of a sex-related hormone in the allantoic fluid of the bird egg, and then determining the gender of the bird within the egg from the presence of an elevated level of a sex-related hormone therein. The sex-related hormone is an estrogen. The method is carried out on chicken eggs prior to or during transfer of the eggs from incubator to hatcher.

Known methods of determining the gender of birds in ovo are considered too slow, too impractical and too unreliable for industrializing purposes.

SUMMARY OF THE INVENTION

The present invention seeks to provide a method for producing chicken wherein the determining the gender of chicken embryo's is more reliable, and suitable for application on industrial scale.

In addition, the present invention seeks to provide a method for producing chicken including the determining the gender of chicken embryo's, wherein a problem with known methods is at least partly solved.

Moreover, the present invention seeks to provide an alternative method for producing chicken including the determining the gender of chicken embryo's.

According to the present invention, therefore a method for producing poultry, in particular chicken is provided, the method comprising;
a) incubating a batch of eggs in an incubating device during a first incubating period of between about 7 to about 11 days, and then,
b) maintaining an egg in a predetermined sampling position during a settling time for allowing allantoic fluid to surface,
c) determining a location of entry based on one or more egg parameters, the egg parameters being an egg dimension, a length along a longitudinal axis of the egg, an egg colour, an image of the egg, a heat image of the egg, a weight of the egg, a perimeter measurement of the egg, incubation time, age of parent stock, and
d) taking an allantoic fluid sample from the egg at the determined location of entry,
e) determining the gender of the chicken poultry in the egg based on the presence of a gender specific compound in the allantoic fluid sample,
f) repeat step b to e for each egg of the batch of eggs,
g) based on the gender of a chicken embryo, dividing the batch of eggs into at least a male batch portion and a female batch portion,
h) incubating at least one of the female batch portion and male batch portion in the incubating device during a second incubating period.

Determining of the location of entry based on one or more egg parameters, the egg parameters being an egg dimension, a length along a longitudinal axis of the egg, an egg colour, an image of the egg, a heat image of the egg, a weight of the egg, a perimeter measurement of the egg, incubation time, age of parent stock, and d) taking an allantoic fluid sample from the egg at the determined location of entry, results in a better allantoic fluid sample and a more reliable determination of the gender of the chicken embryo. This avoids false outcomes which is important because this may lead to direct loss. The desired location of entry is specifically at a point where the allantoic fluid is present in ample quantity and importantly remote from the air cell of the egg, thus not in or on the edge of the air cell of the egg.

The length of the first incubating period is between about 7 to about 11 days, however it will be clear that important is that a) the first incubating period has such a length that the presence of a gender specific compound is reliably detectable, and b) such that the nervous system of an embryo has not yet reached a development stage in which the embryo is able to perceive pain.

The location of entry refers to a position on the surface of the eggshell. This is the position where a sample needle will puncture the shell and enter the interior of the egg in order to take a sample of allantoic fluid.

A sample needle should be chosen such that the strength and durability of the needle are in accordance with its functions i.e. puncturing the egg shell of a large number of eggs, extracting allantoic fluid from the egg, expelling the sample and being cleaned quickly and efficiently. Furthermore the needle should have a smallest possible diameter to prevent unnecessary opening of the egg which would enable unwanted effects onto the hatching egg like intrusion of bacteria or loss of fluids by leaking or evaporation. Furthermore a sample needle should be able to contain the required amount of allantoic fluid. Furthermore a needle should be able to suction fluid without false air, thus using a perfect vacuum. This is in contrast with other solutions that require a needle, syringe and/or hose using negative air pressure. These other solutions suffer from remaining air in the system that will influence the allantoic fluid sample. A preferable sample needle has a diameter of 0.5 to 0.8 mm with a plunger that extends through the needle at least to the needle tip.

The allantoic fluid typically is an excretory medium for the nitrogenous metabolites of an avian embryo. The allantoic fluid begins to form around day 3 of incubation, as disclosed by Hamburger, V and Hamilton, HL (1951)."A series of normal stages in the development of the chick embryo". Journal of Morphology 88 (1):49-92.

Some steps relate to handling of a separate egg and will be repeatedly executed for each egg of the batch. The repetition can be in parallel and/or in series or in other words simultaneous and/or subsequent. The invention is most beneficial when the steps are repeated with each and all eggs of the batch of eggs. However, if desired the steps can be repeated with only a portion of the eggs of the batch of eggs with, as will be clear, a loss of benefit.

It will be clear that preferably all steps are performed at a hatchery. It may be conceivable that one or more steps are at least partly performed outside the hatchery.

In the second incubating period, a different of the same incubating device may be used. After step h), eggs are normally transferred to a hatching device where the eggs are hatched until hatching occurs.

The invention relates to producing poultry like chicken, turkey and ducks or any other species. In the remainder of the text, reference is made to chicken or chicks. It will be clear however that the invention is not limited to chicks.

In an embodiment of the method, the settling time is at least 5 minutes, preferably between 5 and 15 minutes. The allantoic fluid has then the opportunity to surface or on other words to heap up, or accumulate at a desired location within the egg.

In an embodiment of the method wherein the sampling position comprises a position in which the egg is tilted with a blunt side of the egg upwards and such that the longitudinal axis of the egg makes a predefined angle $\alpha$ with the vertical, preferably an angle $\alpha$ of about 45°. This tilting may increase a possible target area where an allantoic fluid sample can be taken.

In an embodiment of the method, step d) comprises moving a sample needle along a line of travel, wherein the line of travel makes an angle with the longitudinal axis of the egg, preferably the line of travel is vertical at the location of entry, more preferably the line of travel is transverse with respect to the egg shell at the location of entry. The line of travel preferably is a rectilinear line of travel. The line of travel being transverse with respect to the egg shell at the location of entry, facilitates puncture of the egg shell. In an embodiment of the method, step d) comprises aligning the longitudinal axis of the sample needle with the line of travel.

In an embodiment of the method, the egg is secured in the sampling position such that the egg does not move while the sample needle engages the egg. This facilitates to meet high precision requirements.

In an embodiment of the method, step c) consists of determining the length dimension of the egg along the longitudinal axis of the egg and based on the length dimension determine the location of entry through an egg shell for a tip of the sample needle. The length dimension is the length between the top and the bottom of the egg. The top and the bottom of the egg lie on the central longitudinal axis of the egg. Determining the location of entry based on one determined parameter of an egg, that is the length dimension of the egg along the longitudinal axis of the egg, reduces the amount of required equipment while still performing in terms of successful samples taken. Reducing the amount of required equipment is important in view of the massive amount of eggs that need to be processed like for example 500 eggs per hour for a small commercial hatchery.

In an embodiment of the method, step d) comprises positioning a plunger forward in the tip of the sample needle prior to insertion of the sample needle into the egg. This facilitates the taking in of the allantoic fluid sample in that no false air is between the sample and the plunger and the amount of sample taken is more predictable. Preferably, the plunger protrudes slightly out of the sample needle such that the plunger promotes puncture of the egg shell. The plunger may have a pointy tip to promote puncture of the egg shell even more.

In an embodiment of the method, the tip of the sample needle has a diameter configured to puncture an egg shell and as small as possible to minimize a hole in the egg, in particular the diameter of the tip of the needle is between 0.5 to 0.8 mm.

In an embodiment of the method, the tip of the sample needle has a cone shape having a cone angle between 10° and 40°, preferably a cone angle of about 18°. This even more promotes puncture of the egg shell.

In an embodiment of the method, step d) comprises determining the degree of penetration of the tip of the sample needle into an interior of the egg. This even more results in a better allantoic fluid sample and a more reliable determination of the gender of the chicken embryo.

In an embodiment of the method, step d) comprises detecting the start of penetration of the tip of the sample needle into the interior of the egg. This enables improved control of the degree of penetration of the tip of the sample needle into an interior of the egg. This even more results in a better allantoic fluid sample and a more reliable determination of the gender of the chicken embryo. The start of penetration of the tip of the sample needle into the interior of the egg is the very moment that the egg shell is punctured and the tip of the sample needle enter the interior of the egg.

In an embodiment of the method, step d) comprises adjusting the degree of penetration of the tip of the sample needle between 2 to 5 mm based on one or more egg parameters, the egg parameters being an egg dimension, a length along a longitudinal axis of the egg, an egg colour, an image of the egg, a heat image of the egg, a weight of the egg, a perimeter measurement of the egg, incubation time, age of parent stock. This even more results in a better allantoic fluid sample and a more reliable determination of the gender of the chicken embryo.

In an embodiment, the method comprises detecting if the amount of allantoic fluid sample is above a predetermined minimum level. This enables to take corrective actions before analysing the allantoic fluid sample. Detecting the amount of allantoic fluid sample may comprise imaging, measuring electrical conductance and/or conductivity for sound or a chemical detection using a colouring agent.

In an embodiment, the method comprises repeatedly taking an allantoic fluid sample from the egg at the determined location of entry or at a location remote from the determined location of entry, like 2 to 6 mm from the determined location of entry. This enables to obtain a better allantoic fluid sample and a more reliable determination of the gender of the chicken embryo while avoiding unnecessary puncturing of the egg because the same location of entry is used. This repeatedly taking a sample as described is possible because of the use of robot technology in the form of a multi-axis robot arm.

In an embodiment, the method comprises analysing the allantoic fluid sample to detect a gender-specific compound, differentiating a male from female embryo, and correlating the gender with the egg. The gender being correlated with the egg enables to make a gender base selection. The gender is correlated or coupled with the egg in any suitable manner.

In an embodiment, the method comprises placing the allantoic fluid sample in a sample holder associated with the sampled egg. The association, coupling or correlation of the sample holder with the sampled egg can be done in any suitable manner like using identifications or registers for sample holders.

In an embodiment, the method comprises providing a visual gender indicator, preferably on or near the egg. This enables to provide information regarding gender independent from an electronic database.

In an embodiment, the method comprises comparing the visual gender indicator with a visual reference, in particular comparing the visual gender indicator with the visual reference regarding one or more of colour, intensity and absorbance.

In an embodiment of the method, the visual reference comprises a sample of a defined threshold fluid.

In an embodiment, the method comprises providing the visual gender indicator on the egg at the location of entry, wherein the visual gender indicator closes a sample hole at the location of entry. This avoid possible ingress of dirt and germs into the interior of the egg.

In an embodiment of the method, the visual gender indicator comprises a contrasting colour. This facilitates visual perception even more.

In an embodiment, the method comprises handling the sample needle by a multi-axis robot arm. This enables to position the sample needle at the location of entry with high precision, in particular with such precision that repeatedly taking an allantoic fluid sample from the egg at one and the same location of entry is possible.

In an embodiment, the method comprises each time cleaning a sample needle before step d).

In an embodiment, the method comprises autonomous replacing a sample needle based on one or more needle parameters, the needle parameters comprising; number of samples taken, lifetime, needle dimension, a percentage of successful taken samples.

In an embodiment of the method, a total lead time between step a) and h) is predetermined for example about 12 or 24 hours. The method runs autonomous, using automated buffers, without the need or interference of an operator. Between step a) and h) is in other words steps b, c, d, e, f and g.

In an embodiment, the method comprises executed steps b, c, d, e, f and g in a climate conditioned space.

In an embodiment, the method comprises handling eggs individually and/or batch wise.

According to the present invention, therefore a hatchery is provided, the hatchery comprising a system for taking an allantoic fluid sample from an egg, the system comprising;
- an egg handling system for maintaining the egg in a predetermined sampling position,
- a sensor system for determining one or more egg parameters, the egg parameters comprising egg dimension, a length along a longitudinal axis of the egg, an egg colour, an image of the egg, a heat image of the egg, a weight of the egg, a perimeter measurement of the egg, a liveability detection of the egg, an activity detection of the egg,
- a sample needle handling system to move a tip of the sample needle to a location of entry,
- a control unit in connection with the egg handling system, the sensor system and the sample needle handling system, and configured to determine the location of entry based on the predetermined sampling position and the egg parameter.

In an embodiment, the hatchery comprises a buffer device to buffer eggs and arranged, based on a process flow, downstream and/or upstream with respect to the system for taking an allantoic fluid sample from an egg.

In an embodiment of the hatchery, the sample needle handling system comprises a plurality of multi-axis robot arms.

SHORT DESCRIPTION OF DRAWINGS

Figure 2:
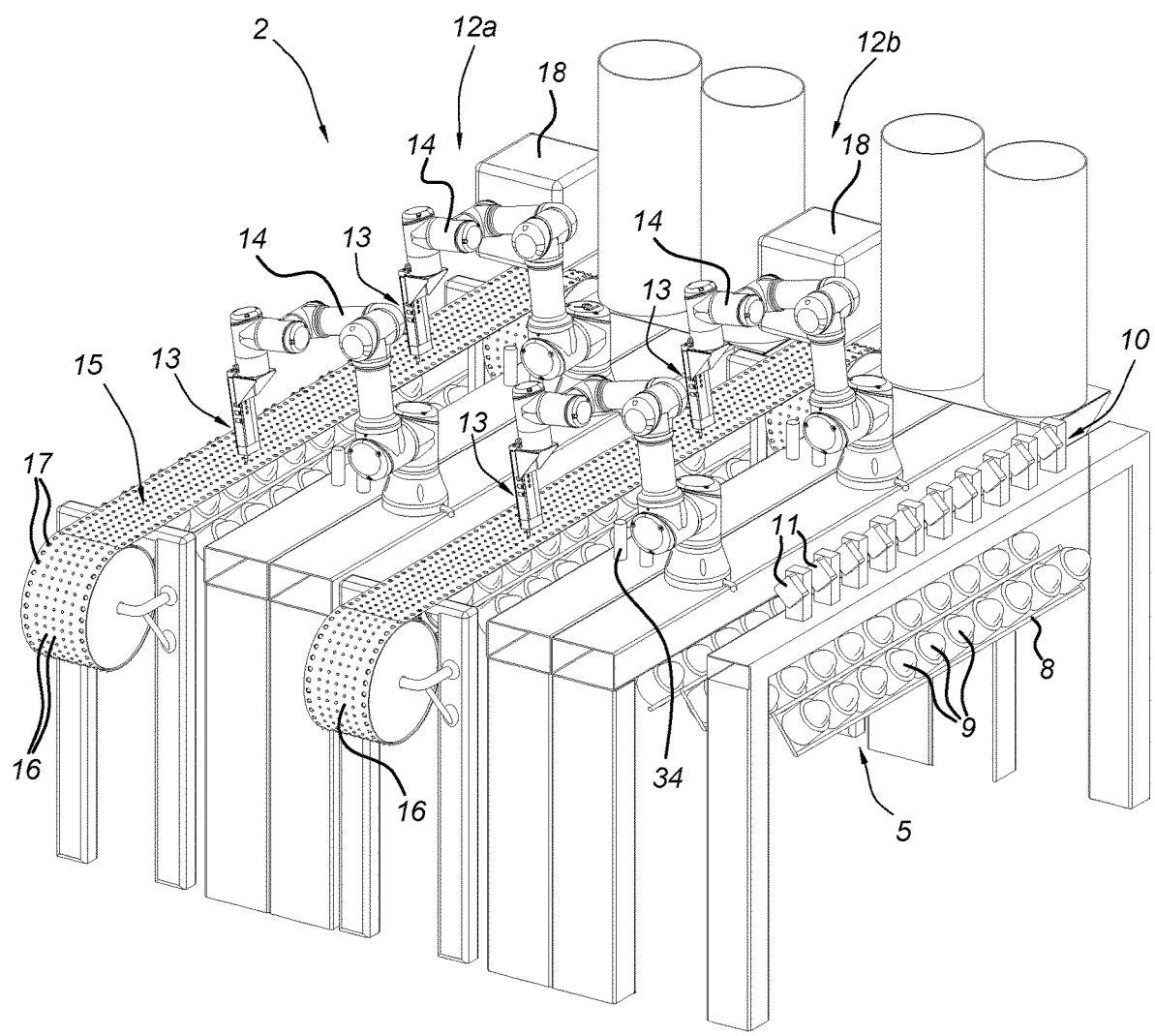
Figure 3:
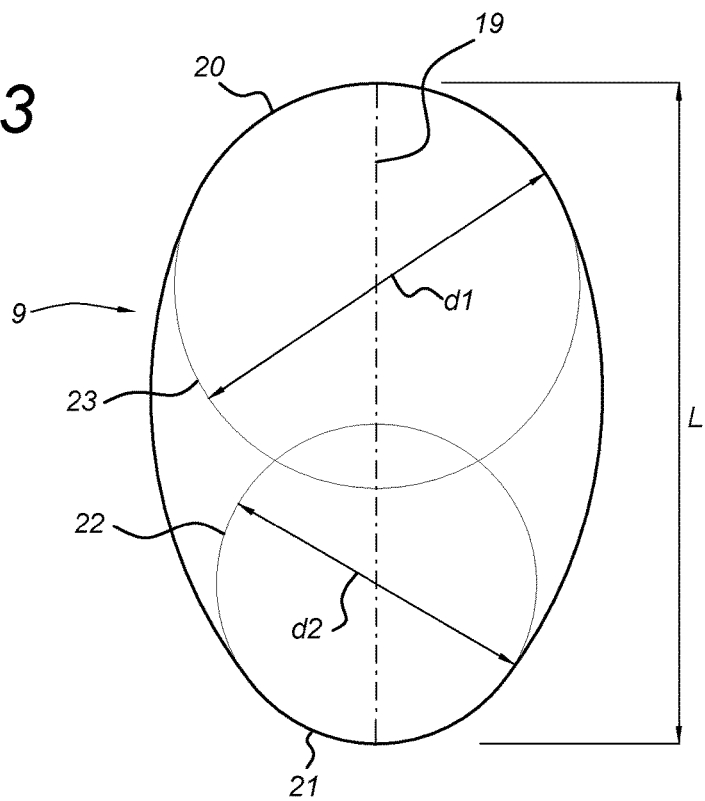
Figure 4:
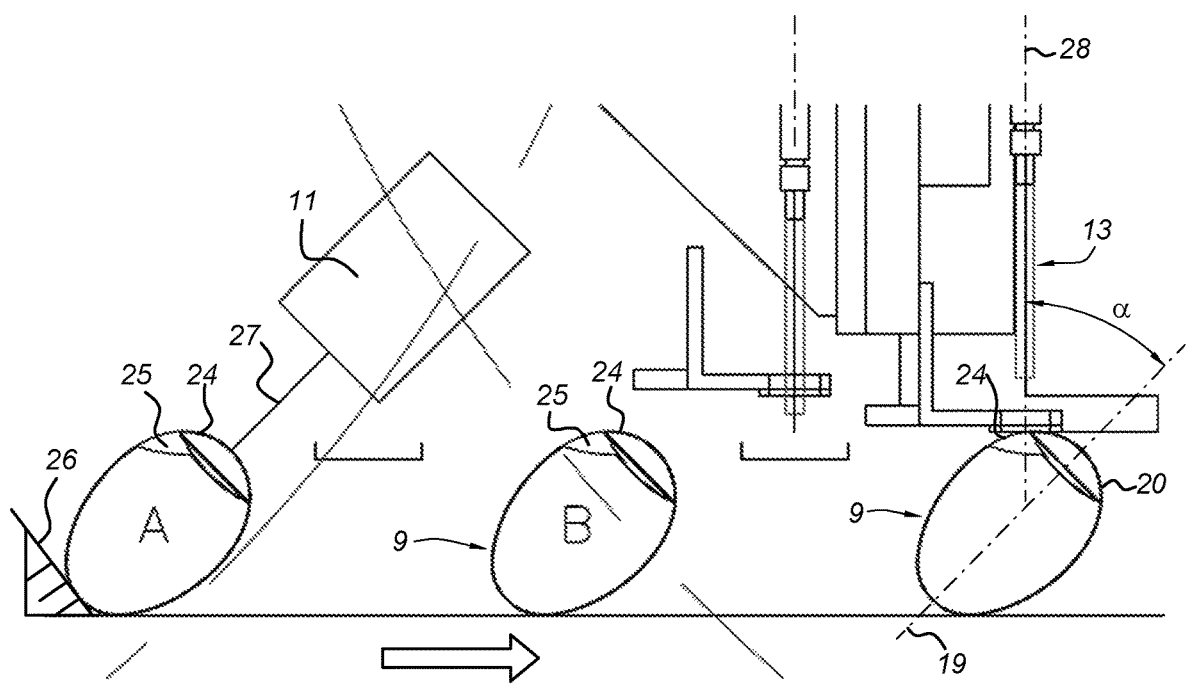
Figure 5:
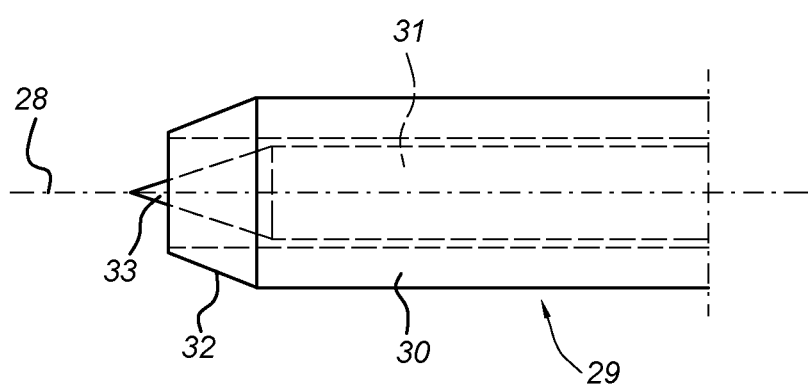

The present invention will be discussed in more detail below, with reference to the attached drawings, in which FIG. 1 is a side view of a process line for use in the method according to the invention, FIG. 2 is a perspective view of a detail of FIG. 1, FIG. 3 is a side view of an egg, FIG. 4 is a schematic side view of a detail of FIG. 2, and FIG. 5 is a side view of another detail of FIG. 2.

DESCRIPTION OF EMBODIMENTS

FIG. 1 is a side view of a process line 1 in a hatchery for use in the method according to the invention.

The hatchery, or better the process line 1 of the hatchery, comprises a system 2 for taking an allantoic fluid sample from an egg. This system 2 will be described below referring to FIG. 2. The process line 1 comprises a buffer device 3a, 3b to buffer eggs. The buffer device 3a, 3b comprises an upstream buffer station 3a and an downstream buffer station 3b. The upstream and downstream arrangement of the upstream buffer station 3a and the downstream buffer station 3b refers to the system 2 for taking an allantoic fluid sample from an egg and the process flow direction 4 of the process line 1. The process line 1 comprises a egg conveyer 5, in this case a belt type conveyer, to transport eggs in the process flow direction 4. Each buffer station 3a, 3b comprises an egg handling system 6 to transfer eggs from the buffer station 3a, 3b to the egg conveyer 5 and vice versa. The egg handling system 6 comprises a, here a plurality of, multi-axis robot arms 7. The total lead time from including the upstream buffer station 3a to and including the downstream buffer station 3b is predetermined and for example about 24 hours. The process line 1 runs autonomous, without the need or interference of an operator FIG. 2 is a perspective view of a detail of FIG. 1. The detail shows the system 2 for taking an allantoic fluid sample from an egg. The system 2 comprises an egg 9 handling system 8, which is schematically shown, for maintaining the egg in a predetermined sampling position. A plurality of consecutive egg handling systems 8 is coupled with the egg conveyer 5 in order to move with the egg conveyer 5. The system 2 comprises a sensor system 10 for determining one or more egg parameters. The sensor system 10 comprises a plurality of sensor devices 11. The sensor devices 11 are distributed along a width of the egg conveyer 5. Therefore a row of eggs 9 can be measured simultaneously by the sensor system 10. The eggs 9 are firmly held by the egg handling system 8, at least during the process at the system 2. In this case, the sensor device 11 measures a length dimension of the egg 9 as will be explained referring to FIG. 5.

The system 2 comprises a, in this case two, sample needle handling systems 12a, 12b. The sample needle handing system moves a tip of the sample needle 13 to a location of entry at the shell of an egg. Each egg handling system 12a, 12b comprises in this case 2 multi-axis robot arms 13. The sample needle 13 is secured to a free end of the robot arm 13. This enables to position the sample needle 13 at the location of entry with high precision. It even enables repeatedly taking an allantoic fluid sample from the egg 9 at one and the same location of entry.

The system 2 comprises a sample handling unit 15. The sample handling unit 15 processes the samples and couples a sample to its associated egg where the sample was taken from. Therefore, the sample handling unit 15 comprises a conveyer 16 with a number of sample holders 17.

The system 2 comprises a control unit 18. The control unit or units, control the system 2 for taking an allantoic fluid sample from an egg. The control unit 18 is operationally coupled with the egg handling system 8 through the conveyer 5. The control unit 18 is operationally coupled with the sensor system 10 and the sample needle handling system 12a, 12b. The control unit 18 is configured to determine the location of entry based on the predetermined sampling position of the egg 9 and an egg dimension, in this case a length along a central longitudinal axis of the egg, obtained by a sensor device 11 of the sensor system 10. The control unit 8 keeps track of the association, coupling or correlation of the sample of allantoic fluid with the sampled egg in any suitable manner like using identifications or registers for sample holders.

The system 2 comprises a cleaning unit 34. This allows to clean a sample needle 13 before taking an allantoic fluid sample from the egg 9 at the determined location of entry FIG. 3 is a side view of an egg 9. A simplified model of the egg 9 is explained based on this figure. The egg is described with a length l along the central longitudinal axis 19 of the egg, a first circle 23 with a diameter d1 and a second circle 22 with a diameter d2. Both circles 23, 22 are within the periphery of the egg 9, in other words are inscribed circles 23, 22. The first circle 23 touches the egg at the blunt side 20 of the egg 9. The second circle 22 touches the egg 9 at a pointed side 21 of the egg 9. As explained in connection with FIG. 2, the length l along the central longitudinal axis 19 of the egg 9 is obtained by a sensor device 11 of the sensor system 10. The diameter is d1 a pre-set value. Therefore, based on only one measurement, the point of entry is accurately determined based on the length l and the diameter d1. As an option, d1 can be made dependent from the length l through an algorithm or a lookup table. However, also in that case only one egg parameter needs to be determined.

FIG. 4 is a schematic side view of a detail of the process line 1 of FIG. 1. This FIG. 4 explains in more detail the taking of an allantoic fluid sample from the egg 9 at the determined location of entry 24. The egg 9 is maintained in the predetermined sampling position. Maintaining an egg 9 in the predetermined sampling position during a settling time allows allantoic fluid 25 to surface. In the sampling position, the egg is tilted such that the longitudinal axis 19 of the egg makes an angle a of about 45° with the vertical. Here, a schematically shown stop 26 defines the position of the egg 9 along the central longitudinal axis 19 of the egg 9. In the figure, the egg 9 is moved to the right during the process. Firstly, the length l along the central longitudinal axis 19 of the egg 9 is obtained by a sensor device 11 of the sensor system 10. Then the egg 9 is moved within reach of the sample needle handling systems 12a, 12b. The sample needle handing system moves a tip of the sample needle 13 to the location of entry 24 at the shell of the egg 9. The sample needle 13 is moved along a line of travel 28, here the vertical. The line of travel makes an angle a of about 45° with the longitudinal axis of the egg. The line of travel 28 is transverse with respect to the egg shell at the location of entry 24. The line of travel 28 is a rectilinear line of travel. The longitudinal axis of the sample needle is aligned with the line of travel 28.

The degree of penetration of the tip of the sample needle 13 into an interior of the egg can be controlled or in other words measured and determined. This is possible because of the use of robot arms 14 as shown. This control may involve detecting the start of penetration of the tip of the sample needle 13 into the interior of the egg 9. The degree of penetration of the tip of the sample needle 13 is e.g. adjusted between 2 to 5 mm based on the length l of the egg 9 along a longitudinal axis 19 of the egg 9.

FIG. 5 is a side view of another detail of FIG. 2. FIG. 4. shows a tip 29 of the sample needle. The plunger 31 is moveably fitted in the sheathing 30 of the needle. The plunger 31 has a pointy tip 33. The tip 29 of the sample needle has a cone shape 32 having a cone angle of about 18. The pointy tip 33 of the plunger 31 has a similar cone shape as shown. The plunger 31 protrudes slightly out of the tip 29 of the sample needle, as shown.

As an example a method for producing chicken is according to the invention is described referring to all figures. The method comprises step a) of incubating a batch of eggs in an incubating device during a first incubating period of between about 7 to about 11 days. Then b) all of the eggs 9 of the batch of eggs are maintained in a predetermined sampling position as shown in FIG. 4. The eggs are maintained in a predetermined sampling position during a settling time. The settling time allows the allantoic fluid to surface. The settling time is at least 5 minutes.

A location of entry 24 is determined based on a measured length l along a longitudinal axis 19 of the egg 9. Then an allantoic fluid sample is taken from the egg 9 at the determined location of entry 24. Using the sample of allantoic fluid, the gender of the chicken embryo in the egg is determined based on the presence of a gender specific compound in the allantoic fluid sample. This step is known per se. For each egg 9 of the batch of eggs the above steps are repeated. The repetition is partly simultaneously like row by row as shown in connection with the sensor system 10, or individually by using a robot arm 14. After determining the gender of each egg 9 of the batch of eggs, the batch of eggs is divided into at least a male batch portion and a female batch portion based on the gender of a chicken embryo. Finally, the female batch portion is incubated during a second incubating period.

The present invention has been described above with reference to a number of exemplary embodiments as shown in the drawings. Modifications and alternative implementations of some parts or elements are possible, and are included in the scope of protection as defined in the appended claims.

The invention claimed is:

1. A method for producing poultry, in particular chicken, the method comprising;
   a) incubating a batch of eggs in an incubating device during a first incubating period of between about 7 to about 11 days, and then,
   b) maintaining an egg in a predetermined sampling position during a settling time for allowing allantoic fluid to surface,
   c) determining a location of entry for each egg based on one or more egg parameters obtained by a sensor system, the egg parameters being an egg dimension, a length along a longitudinal axis of the egg, an egg colour, an image of the egg, a heat image of the egg, a weight of the egg, a perimeter measurement of the egg, incubation time, age of parent stock, and
   d) taking an allantoic fluid sample from the egg at the determined location of entry,
   e) determining the gender of the poultry embryo in the egg based on the presence of a gender specific compound in the allantoic fluid sample,
   f) repeating steps b) to e) for each egg of the batch of eggs, g) based on the gender of a chicken embryo, dividing the batch of eggs into at least a male batch portion and a female batch portion, and
h) incubating at least one of the female batch portion and male batch portion in the incubating device during a second incubating period.

2. The method according to claim 1, wherein the settling time is at least 5 minutes and/or wherein the sampling position comprises a position in which the egg is tilted with a blunt side of the egg upwards and such that a longitudinal axis of the egg makes a predefined angle α with vertical.

3. The method according to claim 1, wherein step d) comprises moving a sample needle along a line of travel, wherein the line of travel makes an angle with the longitudinal axis of the egg.

4. The method according to claim 3, wherein in the sampling position the egg is secured such that the egg does not move while the sample needle engages the egg and/or wherein step d) comprises aligning the longitudinal axis of the sample needle with the line of travel.

5. The method according to claim 3, wherein step c) consists of determining the length dimension of the egg along the longitudinal axis of the egg and based on the length dimension determine the location of entry through an egg shell for a tip of the sample needle.

6. The method according to claim 3, wherein step d) comprises positioning a plunger forward in the tip of the sample needle prior to insertion of the sample needle into the egg.

7. The method according to claim 3, wherein the tip of the sample needle has a diameter configured to puncture an egg shell and as small as possible to minimize a hole in the egg, with a diameter of the tip of the needle being between 0.5 to 0.8 mm and/or the tip of the sample needle has a cone shape having a cone angle between 10° and 40°.

8. The method according to claim 3, wherein step d) comprises determining the degree of penetration of the tip of the sample needle into an interior of the egg and/or detecting the start of penetration of the top of the sample needle into the interior of the egg.

9. The method according to claim 8, wherein step d) comprises adjusting the degree of penetration of the tip of the sample needle between 2 to 5 mm based on one or more egg parameters, the egg parameters being an egg dimension, a length along a longitudinal axis of the egg, an egg colour, an image of the egg, a heat image of the egg, a weight of the egg, a perimeter measurement of the egg, incubation time, and age of parent stock.

10. The method according to claim 1, comprising detecting if the amount of allantoic fluid sample is above a predetermined minimum quantity.

11. The method according to claim 1, comprising repeatedly taking an allantoic fluid sample from the egg at the determined location of entry or at a location remote from the determined location of entry and/or placing the allantoic fluid sample in a sample holder associated with the sampled egg.

12. The method according to claim 1, comprising analysing the allantoic fluid sample to detect a gender-specific compound, differentiating a male from female embryo, and correlating the gender with the egg.

13. The method according to claim 1, comprising providing a visual gender indicator.

14. The method according to claim 13, comprising comparing the visual gender indicator with a visual reference, in particular comparing the visual gender indicator with the visual reference regarding one or more of colour, intensity and absorbance.

15. The method according to claim 14, wherein the visual reference comprises a sample of a defined threshold fluid.

16. The method according to claim 13, comprising providing the visual gender indicator on the egg at the location of entry, wherein the visual gender indicator closes a sample hole at the location of entry and/or wherein the visual gender indicator comprises a contrasting colour.

17. The method according to claim 1, comprising handling the sample needle by a multi-axis robot arm and/or each time cleaning a sample needle before step d).

18. The method according to claim 1, comprising autonomously replacing a sample needle based on one or more needle parameters, the needle parameters comprising: number of samples taken, lifetime, needle dimension, and a percentage of successful taken samples.

19. The metho of claim 1, wherein the predetermined sampling position is a position in which the egg is tilted.

20. A hatchery comprising a system for taking an allantoic fluid sample from an egg, the system comprising
an egg handling system for maintaining the egg in a predetermined sampling position,
a sensor system for determining one or more egg parameters while the eggs are in the predetermined sampling position, the egg parameters comprising egg dimension, a length along a longitudinal axis of the egg, an egg colour, an image of the egg, a heat image of the egg, a weight of the egg, a perimeter measurement of the egg, a liveability detection of the egg, an activity detection of the egg,
a sample needle handling system to move a tip of the sample needle to a location of entry, and
a control unit in connection with the egg handling system, the sensor system and the sample needle handling system, and configured to determine the location of entry based on the predetermined sampling position and the egg parameter.

* * * * *